United States Patent [19]

Magar et al.

[11] 4,116,798
[45] Sep. 26, 1978

[54] REFERENCE ELECTRODE FOR USE AT HIGH TEMPERATURES AND PRESSURES

[75] Inventors: Ingrid Joan Magar, Tuxedo; Patrick Evan Morris, Warwick, both of N.Y.

[73] Assignee: The International Nickel Company, Inc., New York, N.Y.

[21] Appl. No.: 807,052

[22] Filed: Jun. 16, 1977

Related U.S. Application Data

[63] Continuation-in-part of Ser. No. 659,642, Feb. 20, 1976, abandoned.

[51] Int. Cl.² .............................................. G01N 27/30
[52] U.S. Cl. .................................................. 204/195 F
[58] Field of Search ............... 204/195 F, 195 G, 1 T, 204/1 H

[56] References Cited

U.S. PATENT DOCUMENTS

| | | | |
|---|---|---|---|
| 3,152,058 | 10/1964 | Hutchinson et al. | 204/196 |
| 3,272,731 | 9/1966 | Hutchinson et al. | 204/195 F |
| 3,530,056 | 9/1970 | Haddad | 204/195 F |
| 3,575,834 | 4/1971 | Hoole et al. | 204/195 F |
| 3,790,463 | 2/1974 | Gealt | 204/195 F |
| 3,793,176 | 2/1974 | Jerrold-Jones | 204/195 F |

OTHER PUBLICATIONS

Vermilyea et al., "J. Electrochemical Soc.", vol. 119, No. 1, 1972, pp. 39-43.

*Primary Examiner*—T. Tung
*Attorney, Agent, or Firm*—Ewan C. MacQueen; Raymond J. Kenny; Walter A. Petersen

[57] ABSTRACT

The invention relates to an improved silver/silver-chloride reference electrode adapted for use in aqueous corrodent solutions at high temperatures and high pressures. The reference electrode provides a useful standard for measuring electrochemical phenomena related to the corrosion process so that metals can be compared on a thermodynamically useful scale. The formation of bubbles within the reference electrode, which can cause open circuit conditions, is substantially avoided by equalization of internal and external pressure through the use of a heat sealing vent means within the electrode body. Ionic conduction between the electrolyte contained within the reference electrode and the corrodent solution is controlled by a bridge containing tightly gripped fibers which are subjected to additional compression during heating and subsequent pressurization.

6 Claims, 1 Drawing Figure

U.S. Patent
Sept. 26, 1978
4,116,798
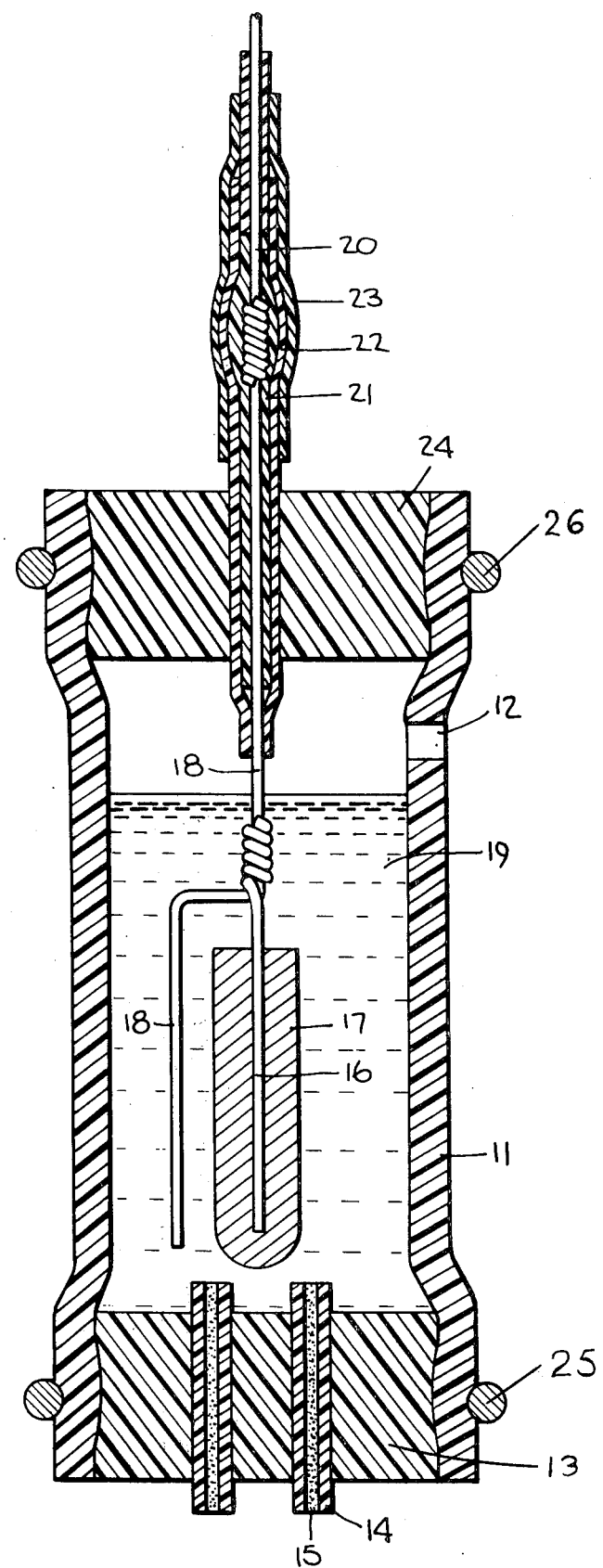

REFERENCE ELECTRODE FOR USE AT HIGH TEMPERATURES AND PRESSURES

The present invention is a continuation-in-part of application Ser. No. 659,642, filed Feb. 20, 1976, now abandoned.

The invention relates to a reference electrode, and more particularly, to a silver/silver-chloride reference electrode useful for electrochemical corrosion measurements in high-temperature, high-pressure corrodent solutions.

With the advent of electrical power generating systems that operate at increasingly higher temperatures and pressures, it has become desirable to measure electrochemical phenomena related to the corrosion processes occurring in such systems. Metals immersed in aqueous environments form insoluble metal oxide films. The metal oxide films can affect the corrosion behavior of the metal. For example, the nature of the metal oxide film, degree of porosity, composition, stoichiometry, thickness, etc., can affect the potential of the metal surface. These characteristics can be measured by comparing the potential difference between a test piece of the metal and a standard half cell. By providing such a standard reference electrode, it is possible to compare metals on a thermodynamically useful scale. Plots of potential versus time or potential versus the logarithm of current density, e.g., a polarization curve, are useful for studying the corrosion resistance of a metal.

A silver/silver-chloride half cell provides a useful standard for electrochemical measurements. In its simplest form, a silver/silver-chloride half cell can consist of a silver wire having a coating of silver chloride, a relatively insoluble compound, immersed in a dilute aqueous solution of a chloride salt or electrolyte contained within a suitable vessel. An ion-conducting liquid communicating means or bridge provides contact between the electrolyte and a corrodent solution. A lead from the silver wire, which provides an electron-conducting path, is connected to the test piece through an electrometer, a sensitive measuring instrument. The difference in electromotive force is measured with the electrometer.

Measurement of electrode potential in aqueous solutions under conditions of standard temperature and pressure is a relatively simple and straightforward procedure. However, at high temperatures, e.g., 300° C, high pressures, e.g., 14,000 kPa, and relatively long periods of time, e.g., more than two months, the well-known methods of measuring electrode potential are not applicable.

One approach to the problem of measurement of electrode potential in aqueous solutions at high temperatures and pressures is to incorporate the reference electrode into the pressurized environment where it operates under the same conditions as the rest of the electrochemical cell. Because a pressure differential can exist between the pressurized water system and the electrode cavity, prior art silver/silver-chloride electrodes are subject to open circuit conditions, due to bubble formation in the bridge. Such bubbles can form due to agglomeration of absorbed gas or by diffusion of gas through the wall of the bridge to the low-pressure cavity. Also, the pressure differential can lead to collapse of the electrode body.

The electrolyte used in a silver/silver-chloride reference electrode is generally the soluble salt of a chloride in dilute solution. Since the presence of the chloride ion, a contaminant which even in small amounts in the solution being measured, e.g., 5 ppm, can alter a material's corrosion resistance, it is desirable to minimize potential sources of chloride ion. Consequently, the useful life of prior art silver/silver-chloride electrodes is limited by the rapid migration of the chloride ion from the cell cavity through the ion-conducting liquid communicating means to the corrodent undergoing study. The general approach to the problem of chloride ion contamination from the silver/silver-chloride electrode has been to lengthen the liquid/liquid junction or liquid communicating means thereby lengthening the time period required for chloride ions to migrate from the electrode body to the external aqueous environment. This approach is, however, not entirely suitable since the increased length of the bridge increases the probability of open circuit conditions due to bubble formation and substantially increases the electrical resistance of the bridge.

It has now been discovered that a silver/silver-chloride reference electrode having a tightly packed fiber within the liquid/liquid junction, the fiber subjected to further compression during heating, and a heat sealing vent means in the electrode compartment can be usefully employed in high-temperature, high-pressure aqueous environments.

The FIGURE is a cross-sectional view of a silver/silver-chloride reference electrode for electrochemical studies in high-temperature, high-pressure aqueous environments.

Generally speaking, the present invention is a reference electrode adapted for immersion in an aqueous liquid at high-temperature and high-pressure, wherein a tube body having opposite open ends is sealed at one end with a bridge mounting plug and sealed at the opposite end with an electrode mounting plug enclosing a silver wire, a portion of said silver wire having a fused silver chloride bead, said silver wire fixably disposed within said tube body and immersed within a soluble chloride electrolyte solution contained within said tube body, the improvements comprising: a heat sealing vent means in the wall of said tube body positioned above said electrolyte solution; said bridge mounting plug of a heat-expandable heat-resistant plastic; and a corrosion-resistant bridge restraining means circumjacent said tube body opposite the junction of said tube body and said bridge mounting plug, said tube body being made of a heat-expandable plastic, whereby said heat sealing vent means substantially inhibits bubble formation through internal and external pressure equalization during pressurization and heating of said reference electrode, said heat sealing vent means adapted to close during heating to a temperature above about 300° C and whereby heat expansion of said bridge mounting plug against said restraining means directs lateral forces to seal said bridge mounting plug to said tube body and to a pre-shrunk bridge sleeve surrounding bridge fibers while compressing said bridge fibers.

The tube body, bridge mounting plug, electrode mounting plug, and a portion of the liquid communicating means are prepared from plastics selected for chemical inertness and heat-resistance characteristics. Heat-expandable (conventional) and heat-shrinkable polytetrafluoroethylenes (PTFE) are preferred for this use. A heat sealing vent means in the form of at least one hole within the tube body and located above the level of the electrolyte when the electrode axis is vertical serves to equalize a pressure differential that can exist between the tube body and the corrodent liquid containing system in which the reference electrode is immersed. Pressure equalization serves to substantially eliminate bubble formation within the liquid communicating means as well as to prevent the tube body from collapsing as a result of high external pressure. During use of the reference electrode, the test environment is first pressurized and then heated to the service temperature or pressurizes as it is heated to the service temperature. The vent closes and fuses shut during heating to service temperatures above about 300° C, thereby substantially avoiding contamination of the corrodent by the electrolyte contained within the tube body during service. Once the vent is heat sealed, the electrode can be inclined from the vertical, if desired, without leakage from or through the vent.

The liquid communication means or bridge, which serves as an ion-conducting path, can be prepared from a heat-shrinkable plastic tube or sleeve, which, upon heating, shrinks about a fibrous substance contained therein. The fibers are selected for chemical inertness, as well as heat resistance, and should be sufficiently porous to be suited, in the compressed form, for containment of a liquid. Asbestos fibers, preferably in cord form, have been found useful for insertion within the tube.

Referring now to the drawing, the silver/silver-chloride reference electrode can be constructed from a heat-expandable polytetrafluoroethylene (PTFE) tube body 11 such as that available from Chemplast, Inc., and sold as Virgin Teflon Tubing, having opposite open ends and at least one vent means 12 near one end. The vent means can be a hole made with a hypodermic syringe as described further herein. The open ends of the tube body can be expanded by heating to about 350° C and allowing the ends to cool over a forming tool of an appropriate diameter and length (e.g., a 12 mm length of a 10 cm long × 8 mm O.D. tube body is expanded to 10 mm O.D.). A bridge mounting plug 13 is inserted in one end of the tube body. The non-porous bridge mounting plug can be made from an expandable grade of PTFE, such as that available from Chemplast, Inc. The bridge mounting plug has at least one opening to receive a bridge assembly consisting of a bridge sleeve 14 and bridge fibers 15. Although only one hole is required in the bridge mounting plug to receive one bridge assembly, it is preferred that more than one bridge assembly be used to substantially avoid the remote possibility of open circuit conditions resulting from bubble formation and to lower electrical resistivity.

The bridge sleeve can be prepared from a heat-shrinkable grade of PTFE, such as Flexite heat-shrinkable tubing TE-250 available from L. Frank Markel & Sons, Inc., (about 2 mm diameter after shrinking). Chemically pure asbestos, preferably asbestos in the form of commercially manufactured cord that has been fired at temperatures above about 430° C to drive off organic residues, is inserted within the heat-shrinkable PTFE bridge sleeve. The heat-shrinkable PTFE bridge sleeve is heated to about 350° C to shrink the sleeve and tightly surround the bridge fiber. The bridge sleeve containing the bridge fiber is inserted in the bridge mounting plug.

A corrosion-resistant bridge restraining means 25, such as one made from a 16% Cr, 8% Fe, balance Ni alloy wire, is positioned about the tube and securely tightened thereby retaining the bridge mounting plug, bridge sleeve, and bridge fiber within the tube. The material from which the bridge restraining means is prepared is selected to have a coefficient of expansion lower than the coefficient of expansion of the bridge mounting plug, and preferably as well as that of the tube body and bridge sleeve(s) (e.g., the coefficient of expansion of a suitable 16% Cr, 8% Fe, bal. Ni alloy is about $11.5 \times 10^{-6}$ ° C, and the coefficient of expansion of PTFE is about $10^{-4}$ ° C). It is preferred that the coefficient of expansion of the restraining means be at least about $3 \times 10^{-5}$ ° C less than the coefficient of expansion of the bridge mounting plug. During heating to the service temperature, the pre-shrunk bridge sleeve, prepared from heat-shrinkable PTFE, does not shrink further. The bridge mounting plug, which is prepared from a heat-expandable plastic (e.g., PTFE), serves to further compress the bridge sleeve as a result of its expansion which is restricted by the bridge restraining means having a lower coefficient of expansion and, consequently, exhibiting less expansion. Restriction of the expansion of the plug by the restraining means provides a tight seal from the test environment as well as further compaction of the bridge fiber. Examination of reference electrodes after service has revealed deep grooves within the tube and bridge mounting plug that result from the disparity in coefficients of expansion. The fact that the force is directed inwardly against the bridge sleeve and further compresses the bridge fibers is shown by the inwardly-bowed or parabolic cross sectional shape of bridge sleeves removed from reference electrodes after 2 months' service at 300° C. The further compression of the bridge fibers during heating to the service temperature is largely responsible for the long-term reliability of the reference electrode of the present invention.

A silver wire 16 having a fused silver-chloride bead 17, extends within the tube. The silver-chloride bead can be formed by preparing a molten bath, e.g., at 480° C, of silver-chloride contained within a quartz tube closed at one end. The silver wire is inserted in the molten silver-chloride and the quartz tube, silver-chloride and silver wire are allowed to cool to room temperature. The silver wire with fused silver-chloride bead is then removed from the quartz tube.

A supplementary silver wire 18 is spliced to the silver wire above the silver-chloride bead, and the lower portion of the supplementary silver wire runs parallel to the silver-chloride bead. This supplementary silver wire, which will be described further herein, serves to increase the silver surface area exposed to the contained electrolyte 19 and improves electrical contact with the contained electrolyte. The electrolyte used in the reference electrode is generally a soluble chloride salt such as a 0.01 molar solution of potassium chloride in water. The level of the electrolyte is maintained below the level of the vent during operation of the reference electrode, and the electrode is generally used with the longitudinal axis of the tube in the vertical position. The reference electrode can be totally immersed in the liquid environment since at temperatures above about 300° C the vent hole fuses shut after pressure equalization. During heating to the service temperature, expansion of the tube body has been found to compensate for expansion of the contained electrolyte so that the electrolyte level remains relatively constant within the tube body.

The upper portion of the supplementary silver wire 18 (the electron-conducting path) is spliced to a PTFE insulated wire 20 (e.g., silver-plated copper wire), which is connected to a suitable measuring instrument such as an electrometer or vacuum tube voltmeter and thence to a metal test piece also contained within the corrodent solution. The spliced region together with a portion of the supplementary silver wire are enclosed in a first electrode sleeve 21 prepared from a small diameter heat-shrinkable PTFE tube. The first electrode sleeve is heated to about 350° C to shrink it about the splice and supplementary silver wire. A second electrode sleeve 22, of greater length than the first, is placed over the first electrode sleeve. It extends over the PTFE insulated silver-plated copper wire for a short distance above the splice. Below the splice, the second electrode sleeve overlaps the first electrode sleeve extending on the supplementary silver wire to a joint just above the region where the silver wire having the silver chloride bead is spliced. The second electrode sleeve, also prepared from a heat-shrinkable PTFE, is heated to about 350° C to shrink it in place. A third electrode sleeve 23, also prepared from a heat-shrinkable PTFE, of larger diameter than the first and second electrode sleeves, overlaps these sleeves above and below the splice between the PTFE insulated wire and supplementary silver wire and extends to a point just below this splice. The third electrode sleeve is shrunk in place by heating to about 350° C.

The wiring unit comprising PTFE insulated wire, supplementary silver wire, and two electrode sleeves is inserted through a hole in the electrode mounting plug 24, which preferably is prepared from a heat-expandable PTFE, and substantially flush to the third electrode sleeve. The supplementary silver wire is spliced to the silver wire 16 having the fused silver-chloride bead. The end of the supplementary silver wire is preferably extended parallel to the silver chloride bead to promote electrical contact with the electrolyte.

Electrolyte can be added to the assembly just prior to insertion of the electrode mounting plug or after insertion through a previously prepared vent means with a hypodermic syringe having a needle diameter in the range of about 0.3 to about 0.7 mm, e.g., 0.46 mm and selected to provide closure during heating of the heat-expandable plastic tube to temperature above about 300° C.

A corrosion-resistant electrode restraining means 26 is used to secure the electrode mounting plug assembly to the tube body. The electrode restraining means can be prepared from a corrosion-resistant wire (e.g., a wire made from alloy containing 16% Cr, 8% Fe, balance Ni) selected to provide a lower coefficient of expansion than the coefficient of expansion of the electrode mounting plug as well as the tube and plastic portions of the wiring unit in the manner described previously herein for the bridge restraining means and bridge mounting plug. During heating to the service temperature, the lower coefficient of expansion of the electrode restraining means restricts the expansion of the tube and electrode mounting plug assembly and serves to effectively seal these components to each other.

Prior to introduction of electrolyte into the assembly, it is expedient to place the end of the electrode containing the bridge fiber in distilled water. This serves to wet the bridge fiber with a solution substantially free of chloride ion.

In excess of 50 reference electrodes conforming to the foregoing description have been used without failure or measurable contamination of the corrodent test solution it sealed autoclaves operating typically at temperatures of 316° C, pressures of 13,790 kPa, for time periods in excess of two months. The anodic polarization characteristic of Type 304 stainless steels and nickel-chromium-iron alloys at the end of a two-month test period have been found to coincide with the characteristics established initially. These results serve to illustrate and confirm the stability of the reference electrode.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

We claim:

1. A reference electrode adapted for immersion in an aqueous liquid at high-temperature and high-pressure comprising:
    (a) a heat-expandable plastic tube body sealed at one end with a heat-expandable, heat-resistant plastic bridge mounting plug and sealed at the opposite end with an electrode mounting plug enclosing a silver wire, a portion of said silver wire having a fused silver chloride bead, said silver wire fixably disposed within said tube body and immersed within a soluble chloride electrolyte solution contained within said tube body;
    (b) a corrosion-resistant bridge restraining means circumjacent said tube body opposite the junction of said tube body and said bridge mounting plug, said restraining means selected to have a coefficient of expansion lower than the coefficient of expansion of said bridge mounting plug;
    (c) a pre-shrunk bridge sleeve surrounding bridge fibers mounted within said bridge mounting plug, whereby heat expansion of said bridge mounting plug against said bridge restraining means directs lateral forces to seal said bridge mounting plug to said tube body while compressing said bridge fibers, and
    (d) a heat sealing vent means in the wall of said tube body positioned above said electrolyte solution to substantially inhibit bubble formation through internal and external pressure equalization during pressurization and heating of said reference electrode, said heat sealing vent means adapted to close during heating to a temperature above about 300° C.

2. A reference electrode as defined in claim 1, wherein said heat sealing vent means is from about 0.3 mm to about 0.7 mm in diameter.

3. A reference electrode as defined in claim 1, wherein said corrosion-resistant bridge restraining means has a coefficient of expansion at least about $3 \times 10^{-5}$ ° C less than the coefficient of expansion of said bridge mounting plug.

4. A reference electrode as defined in claim 3, wherein said mounting plug is made of polytetrafluoroethylene.

5. A reference electrode as defined in claim 4, wherein said tube body is made of polytetrafluoroethylene.

6. A reference electrode as defined in claim 1, wherein said electrode mounting plug is provided with a corrosion-resistant electrode restraining means circumjacent said tube body opposite the junction of said tube body and said electrode mounting plug whereby heat expansion of said electrode mounting plug against said electrode restraining means directs lateral forces to seal said electrode mounting plug to said tube body and to said silver wire.

* * * * *